United States Patent [19]

Perälampi

[11] Patent Number: 5,496,820
[45] Date of Patent: * Mar. 5, 1996

[54] OPHTHALMIC USE OF S-TIMOLOL HEMIHYDRATE

[76] Inventor: Markku Perälampi, Katajatie 30 B 3, SF-36200 Kangasala, Finland

[ * ] Notice: The portion of the term of this patent subsequent to Jul. 27, 2010, has been disclaimed.

[21] Appl. No.: 97,880

[22] Filed: Jul. 27, 1993

Related U.S. Application Data

[63] Continuation of Ser. No. 910,665, Jul. 8, 1992, abandoned, which is a continuation-in-part of Ser. No. 663,853, filed as PCT/FI89/00196, Oct. 13, 1989, Pat. No. 5,231,095.

[30] Foreign Application Priority Data

Oct. 20, 1988 [FI] Finland ................................. 884838

[51] Int. Cl.$^6$ ................................................ A61K 31/535
[52] U.S. Cl. ................................................ 514/236.2
[58] Field of Search ........................................ 514/236.2

[56] References Cited

U.S. PATENT DOCUMENTS 4,195,085  3/1980  Stone ................................. 424/248.51
4,521,414  6/1985  Chiou et al. ........................... 514/229
5,231,095  7/1993  Perälampi ............................ 514/236.3

OTHER PUBLICATIONS

Perälampi, Chemical Abstract 114:49576J (1990).
Drug Evaluations, 6th ed. (1986), American Medical Assn, pp. 335–337.

*Primary Examiner*—Philip I. Datlow

[57] ABSTRACT

A novel composition and method for making compositions containing S-timolol hemihydrate having the formula:

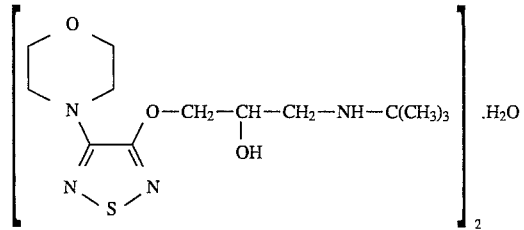

wherein the compositions are useful as pharmaceutical agents for topical administration to an eye for treating glaucoma and/or lowering intraocular pressure.

19 Claims, 1 Drawing Sheet

OPHTHALMIC USE OF S-TIMOLOL HEMIHYDRATE

This application is a continuation of application Ser. No. 07/910,665 filed Jul. 8, 1992 now abandoned, which application is a continuation-in-part of U.S. application Ser. No. 07/663,853 filed Apr. 19, 1991 for NOVEL S-TIMOLOL DERIVATIVE AND PROCESS FOR ITS PREPARATION now U.S. Pat. No. 5,231,095, which was filed as international application no. PCT/FI89/00196 (WO 90/04592) on Oct. 13, 1989, the disclosures of which are expressly incorporated herein by reference.

FIELD OF THE INVENTION

The present invention relates generally to the field of pharmaceutical preparations, more particularly to ophthalmic compositions made from (S)-timolol base, i.e. (S)-1-[(1,1-dimethylethyl) amino]-3-[[4-(4-morpholinyl)-1,2,5-thiadiazol-3-yl]oxy ]-2-propanol, in crystalline form, i.e. in the form of its hemihydrate, as well as to a method for the topical treatment of glaucoma and ocular hypertension by applying such compositions into the eye of a human or an animal in need of such treatment. An alternative nomenclature commonly used in the art to refer to timolol base is 3-morpholino-4-(3-tert-butyl-amino-2-hydroxyporxy)-1,2,5-thiadiazole.

BACKGROUND OF THE INVENTION

β-Adrenergic blockers were first reported to be useful for the treatment of glaucoma in 1967. Since then a vast number of β-blockers have been investigated for ophthalmic use in treating eye disorders such as glaucoma, some of which, e.g. timolol, betaxolol, carteolol, metipranolol, befunolol and levobunolol, have reached clinical use as well. However, all of the compounds currently used for the treatment of humans are associated with a number of side effects, notably cardiovascular, respiratory, central nervous system and ocular side effects (see elg. J. Clin. Pharmacol. 29 (1989) 97).

This is also true of (S)-timolol, which is most commonly sold in its maleate salt form as a drug for the treatment of glaucoma. The (S)-timolol free base in itself is, however, a non-crystalline substance which is generally difficult to handle and to make into accurate dosage forms. Compositions containing, as the active antiglaucoma agent, only (S)-timolol maleate, which is a well-crystallizing substance, as well as their use, are described in the U.S. Pat. No. 4,195,085. In the said compositions timolol base itself without maleate anion is not employed. The presence of the maleate anion is a necessary component of the compositions, but as regards the activity of the preparation is completely superfluous and only constitutes an unnecessary load on the eye.

A further and well known disadvantage of ophthalmic solutions of timolol maleate salt is its sensitivity to light, which imposes strict requirements on the packaging and storage conditions for the maleate salt product, as well as on the carefulness of the patient in handling the product. Furthermore, the presence of the maleate anion may in some formulations have a negative influence on and even destroy the effect of ion-sensitive components.

Use of salt forms such as timolol maleate usually leads to the need of a large amount of additional ions which are delivered into the eye and may cause harmful effects.

SUMMARY OF THE INVENTION

Thus it is an object of the present invention to provide an ophthalmological preparation from a crystalline and sufficiently soluble form of (S)-timolol itself without the additional load and other negative effects of the hitherto used salt anions, and which delivers (S)-timolol to the eye compartment in a sustained and controlled manner with minimum systemic absorption and/or no systemic side effects.

Recently a crystalline form of the (S)-timolol base and its synthesis, namely the (S)-timolol base hemihydrate, was discovered and disclosed in parent application Ser. No. 07/663,853, now U.S. Pat. No. 5,231,095, and its counterpart WO-publication 90/04592. Based on the discovery of its advantageous handling characteristics, therapeutic use of the said (S)-timolol base hemihydrate, particularly topical administration, is discussed in the parent application as being preferred. A detailed discussion of Ophthalmic uses for non-crystalline or non-specified forms of (S)-timolol base in various vehicles has recently been published in Int. J. Pharm., 81 (1992) 59.

According to the present invention it has now surprisingly been discovered that many of the disadvantages involved in the use on the one hand of the (S)-timolol base and on the other hand of the (S)-timolol maleate salt can be avoided by providing an ophthalmic composition containing crystalline (S)-timolol base hemihydrate as the active agent.

DETAILED DESCRIPTION OF THE INVENTION

Figure 1:
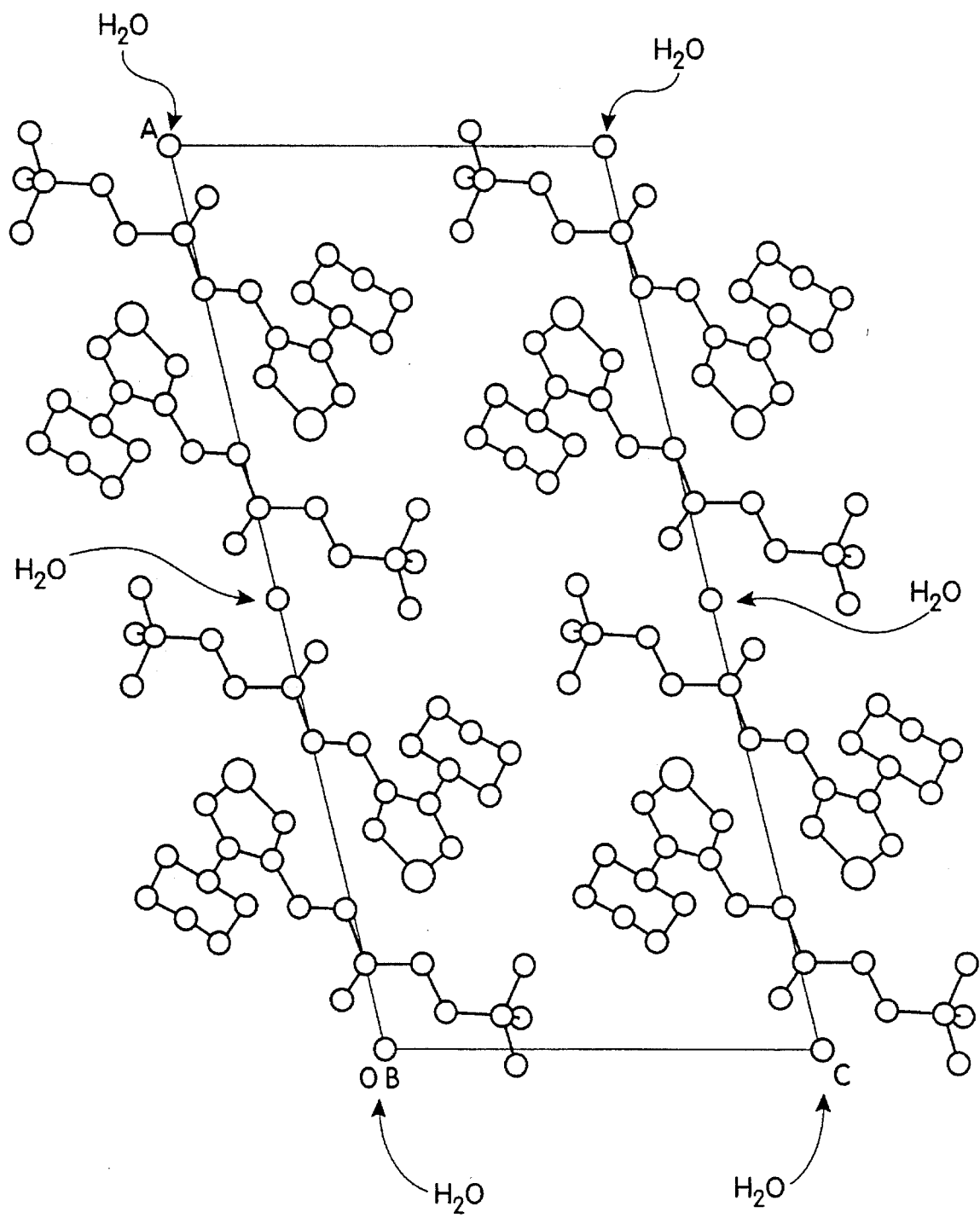
FIG. 1 is a Schematic view of the crystal structure of S-timolol hemihydrate.

According to the invention it is possible to provide a number of novel formulations for eye therapy from the said (S)-timolol base hemihydrate, which formulations have inherently better sustained and controlled effects than those of corresponding formulations made from the (S)-timolol maleate salt. In general, the physical characteristics of the said (S)-timolol base hemihydrate makes it very suitable for the preparation of ophthalmic compositions, and especially in compositions where the base form of (S)-timolol as the active agent without associated maleate is the form of choice, more particularly where the high lipophilicity of the (S)-timolol base hemihydrate is to be made use of.

An illustrative series of physicochemical and in vitro tests have been performed. Preclinical studies with selected conventional or non-conventional formulations of (S)-timolol base hemihydrate have revealed that, in addition to the better physical properties of the base hemihydrate, the formulations according to the invention are at least as well or better suited for eye therapy than formulations made with the (S)-timolol maleate salt. Thus, for example, eye drops made from the base hemihydrate form showed at least similar or even better absorption than those made from the maleate salt. Hence the said preparation is very effective in lowering intraocular pressure after topical application, both in the normal and the glaucomatous eye. In addition formulations according to the invention showed good patient compliance.

Further, the compositions according to the invention show better stability to light than the known timolol maleate salt compositions. Thus, in addition to not having to be protected from light by the patient, which is a clear user's advantage, the light stability of the (S)-timolol base hemihydrate compositions makes it possible to exploit new alternatives in packaging technology for timolol containing products. As compared to timolol maleate, it is more suitable for use with vehicles and devices (such as a unit dose) where transparency of the packaging is necessary or desirable.

As the maleate (or any unnecessary salt load) is missing, the adjustment of pH in compositions containing (S)-timolol base hemihydrate is more easily accomplished, and particularly insofar as the use of an additional base is not necessary and not used, unless otherwise desired for another reason. In the compositions according to the invention, other desired ion-sensitive components can also be used without adversely affecting their desirable properties.

An important aspect in connection with the invention is the fact that crystalline (S)-timolol base hemihydrate can be formed in practically 100% pure form, i.e. the traces of the enantiomeric, less active (R)-form can be completely removed in a single crystallization step, as is disclosed in the parent application Ser. No. 07/663,853 now U.S. Pat. No. 5,231,095 and its corresponding international counterpart WO 90/04592. Thus it is possible to use, in the composition, a purer active agent than can be obtained by the manufacture of the maleate salt, the manner of manufacture of which inevitably leads to the end product containing a disadvantageous amount of the (R)-enantiomer unless it is prepared from a 100% pure (S)-timolol base, e.g. from (S)-timolol base hemihydrate of the present invention, or alternatively unless the (R)-enantioner containing maleate salt is purified by an additional and tedious purification process. Thus the manufacture of the composition is simplified as well and there is no need to make the maleate salt from the base hemihydrate as the timolol base hemihydrate functions at least as well as the maleate salt for the intended purpose.

The present invention thus provides an ophthalmic composition for topical use containing a therapeutically effective amount of pure (S)-timolol base hemihydrate together with an ophthalmic carrier.

A further object of the present invention is to provide a use of (S)-timolol base hemihydrate for the preparation of an ophthalmic composition for topical use, especially for the treatment of glaucoma and ocular hypertension in humans and animals.

A further object of the invention is to provide a method for the preparation of an ophthalmic composition for topical application use or administration to the eye, especially for the treatment of glaucoma and ocular hypertension, wherein a therapeutically effective amount of (S)-timolol base hemihydrate is combined with an acceptable and effective ophthalmic carrier.

The invention further provides a method for the topical treatment of glaucoma and ocular hypertension according to which a therapeutically or pharmaceutically effective amount of (S)-timolol base hemihydrate for treatment of glaucoma and/or ocular hypertension is topically administered to the eye of a human or an animal in need of such treatment.

The compositions according to the invention are particularly suitable for topical use. Examples of such compositions, aqueous or non-aqueous, are solutions, including oils and gels, suspensions, ointments and solid soluble or insoluble ocular inserts and other acceptable drug delivery systems known as such in the art. The concentration of active agent in the composition may vary but lies generally in the range of about 0.01 to to about 5, preferably between about 0.1 and about 2 percent by weight of the total composition. Higher doses such as for example up to about 10 percent by weight, or lower than those mentioned above, can be employed provided the dose is effective in lowering intraocular pressure. A unit dosage form contains typically an amount of 0.001 to about 5.0 mg, preferably about 0.005 to about 2 mg of active agent.

The compositions according to the invention contain at least an ophthalmologically suitable carrier known in the art. In the case of solutions and ointments, such a carrier my be water, a lower alkanol, polyols, polymeric alcohols, petrolatum, physiologically acceptable oils such as silicone oil, mineral oil, white oil and vegetable oils, for example ricin oil, peanut oil and other acceptable carriers, or any mixtures of two or more of the foregoing.

The solid inserts are made from a suitable polymer, such as acrylates, natural products, starch derivatives, other synthetic derivatives, and e.g. cellulose derivatives. A number of such products are commercially available in various molecular weight ranges, and are as such known in the art.

The eye inserts are typically made by mixing the active agent, together with optional additives, with the polymer in question in molten form, and forming of the mixture obtained into inserts of any suitable shape by moulding. An alternative route of manufacture comprises dissolving the components in a suitable solvent and then evaporating the solvent to form the insert, e.g. in the form of a film.

The compositions according to the invention may also contain selected ophthalmologically acceptable adjuvants admixed with the S-timolol hemihydrate active agent, for example (a) to adjust tonicity, such as sodium chloride, potassium chloride, glycerol, mannitol, sorbitol, sodium borate, sodium acetate and the like, (b) to adjust viscosity, such as cellulose derivatives, polyvinylpyrrolidone, polyvinyl alcohol, carboxyvinyl polymers and the-like, (c) to adjust or to stabilize pH, such as conventional bases or acids or buffers, such as phosphate buffers, borate buffer or the like, (d) to increase solubility, and (e) to stabilize and to preserve the preparation, such as quaternary ammonium compounds, phenyl mercuric salts, thiomersal, methyl and propyl paraben, benzyl alcohol, phenylethanol and the like. Preparations without antimicrobial preservatives are provided in unit dose form.

The pH of the composition is suitably from 5 to 8 and most preferably from 6.5 to 7.5 and may be, as mentioned above regulated by adding a suitable buffer, such as a phosphate or borate buffer. The pH of the compositions of solutions, and, where applicable, of suspensions, ointments and inserts, may be adjusted to higher or lower values depending on the nature of the carrier in order to improve the penetration of the active moiety through the liberation thereof from the carrier vehicle, or alternatively the ambient or unregulated pH of the carrier can be employed.

By means of the invention it is thus possible to make a wide range of various compositions, which may be optimized as regards their activity, by selectively choosing suitable carriers and/or adjuvants. The free (S)-timolol base hemihydrate gives wider possibilities for formulation without any limitations as compared to the maleate salt in which the presence and the role of the maleate component of the active agent has to be taken into consideration, such as when using ion-sensitive components.

The following describes non-limiting typical examples of compositions suitable for topical application to the eye for treating glaucoma and ocular hypertension, i.e. lowering intraocular pressure, according to the invention:

EXAMPLE 1

Solution

| Components | Multi dose | Unit dose |
| --- | --- | --- |
| (S)-Timolol base hemihydrate | 2.56 mg | 2.56 mg |
| Benzalkonium chloride | 0.1 mg | — |
| Monosodium phosphate 2H$_2$O | 10.53 mg | 10.53 mg |
| Disodium phosphate 2H$_2$O | 12.01 mg | 12.01 mg |
| Water for injection q.s. | 1.0 ml | 1.0 ml |

The above components are admixed by dissolution in water. The resulting bulk solution is first sterilized by filtration and then filled aseptically into suitable containers.

EXAMPLE 2

Gel

| Components | Multi dose | Unit dose |
| --- | --- | --- |
| (S)-Timolol base hemihydrate | 2.56 mg | 2.56 mg |
| Benzalkonium chloride | 0.1 mg | — |
| Methylcelluse 4000 | 15.0 mg | 15.0 mg |
| Monosodium phosphate 2H$_2$O | 10.53 mg | 10.53 mg |
| Disodium phosphate 2H$_2$O | 12.01 mg | 12.01 mg |
| Water for injection q.s. ad | 1.0 ml | 1.0 ml |

The Methylcellulose is dissolved in a portion of the sterile water and sterilized by autoclaving. All the other constituents are dissolved in a remaining portion of the water and sterilized by filtration. The water solution containing the other constituents is combined aseptically with the methyl cellulose gel.

EXAMPLE 3

Oil

| (S)-timolol base hemihydrate | 2.56 mg |
| --- | --- |
| Ricin oil q.s. ad | 1 ml |

The (S)-timolol base hemihydrate is dissolved in the ricin oil.

EXAMPLE 4

Ointment

| (S)-Timolol base hemihydrate | 2.56 mg |
| --- | --- |
| Petrolatum q.s. ad | 1.0 mg |

The above listed components are aseptically combined.

EXAMPLE 5

Insert

| (S)-Timolol base hemihydrate | 1 mg |
| --- | --- |
| Hydroxypropylcellulose q.s. ad | 12 mg |

The above components are molded together in a known manner to form eye inserts.

(S)-timolol hemihydrate or S-(-)-3-morpholino-4-(3-tert-butyl-amino-2-hydroxyprop oxy)-1,2,5-thiadiazole hemihydrate itself, and its synthesis and its use in treating human or animal disorders such as by topical administration has heretofore been unknown.

It has surprisingly been discovered that S-timolol hemihydrate may be easily crystallized in an unexpected way. This compound, as obtained in a stable crystalline form, and the preparation thereof, are not known from the prior art.

The structure of the compound has been elucidated using X-ray diffraction. The results indicate for the compound a crystal structure wherein four S-timolol base molecules and two water molecules are situated in the same unit cell, the hydrophilic parts (—NH, —OH) of each pair of two S-timolol molecules being arranged around one water molecule. The hydrogen bridges formed by the water molecule and the two polar groups, along with the favorable lipophilic intermolecular forces, existing in the crystal lattice provide for optimal packing of the molecules. Because of the above-mentioned molecular arrangement, S-timolol hemihydrate may be crystallized in an optical purity of 100% e.e., which means that S-timolol hemihydrate and the crystallization procedure may also be used for purification purposes, e.g., small amounts of the corresponding R-timolol enantiomer generally encountered in the starting material prepared by any current method, may be removed completely. The molecular arrangement in the crystal lattice along with easily controlled crystal growth is the reason for this surprisingly simple removal of impurities in one single crystallization step.

The appended FIG. 1 discloses the arrangement of S-timolol hemihydrate in the unit cell, omitting the hydrogen atoms.

The crystal structure for S-timolol hemihydrate (single crystals from water-methylene chloride) was measured with a Enraf-Nonius CAD-4 diffractometer using graphite-monochromatized MoK$_\alpha$ (0.71073 A) and $\omega$–2$\Theta$ method at 21° C. The cell parameters and orientation matrix were determined from 18 reflections (6<$\Theta$<10°). The measuring rate (° min$^{-1}$) was 0.87–16.5, width ($\Theta$) 0.5+ 0.344 tan $\Theta$ and area ($\Theta$) 2–25. The following crystal data were obtained: space group monoclinic, C2 (No. 5); a=23,435(3) A, b=6.384(8) A, c=11.591(1) A, $\alpha$=90.00°, $\beta$=103.081(1)°, $\gamma$=90.00°, V=1687(3) A, Z=2, d=1.281 gcm$^{-3}$.

The results obtained with a NMR spectrometer support the above obtained X-ray diffraction results (Instrument Bruker AC 250/Aspect 3000). $^1$H-NMR (solvent CDCl$_3$)$\delta$(ppm): 1.09 (s, 9H), 2.0 (b, appr. 2.5H), 2.57 (d+d, 1H; 12.0 and 8.0 Hz), 2.80 (d+d, 1H; 12.0 and 4.0 Hz), 3.52 (m, 4H), 3.79 (m, 4H), 3.91 (m, 1H), 4.36 (d+d, 1H; 11.1 and 5.8 Hz), 4.47 (d+d, 1H; 11.1 and 4.1Hz).

$^{13}$C-NMR (solvent CDCl$_3$)$\delta$(ppm): 28.91 (q), 50.24 (s), 44.33 (t), 66.10 (d), 72.76 (t), 153.66 (s), 149.78 (s), 47.78 (t), 66.33 (t).

S-timol hemihydrate has also been analyzed thermogravimetrically (Perkin Elmer, TGS-2 thermo-gravimetric analyzer and attached differential scanning DSC 4 calorimeter). The TG graph indicates splitting off of the hydrate water at about 50° C., the DSC gives a melting point of 53.3° C.

The novel crystalline S-timolol hemihydrate may be prepared in a very simple manner by crystallizing the same from a solution prepared with an aqueous organic solvent or solvent mixture of the S-timolol base. As a starting material, also a salt of the S-timolol base, for example the maleate salt, may be used, whereby the free S-timolol base is first liberated with an alkaline agent, especially with sodium hydroxide, and the hemihydrate is thereafter crystallized as described above. The starting material may contain small amounts of impurities, e.g. in form of the corresponding R-timolol base or the corresponding salt, respectively, which R-enantiomer may be removed completely in a single crystallization step, to give the desired S-timolol hemihydrate in optically pure form.

In the process, any organic solvent or solvent mixture may be used in which the S-timolol base dissolves but in which, in the presence of water, the formed hemihydrate is sparingly soluble. The process is generally carried out by forming a solution of the S-timolol base with an organic solvent. Water is added in an amount sufficent for the formation of the hemihydraft, and the S-timolol hemihydrate is allowed to crystallize. As the organic solvent which dissolves the timolol base, for example, an aromatic hydrocarbon, such as toluene or xylene, especially toluene, an ether-type solvent, such as di-isopropyl ether, an alcohol, such as ethanol, or a chlorinated hydrocarbon, such as methylene chloride, may be used. The solubilities of the timolol base and the hemihydrate may be regulated by means of an additional organic solvent, or in some cases by the amount or ratio of water used. Thus, for example, an aliphatic hydrocarbon, such as hexane, may be used as a solvent component which reduces the solubility of the hemihydrate. In the system, the amount of water may vary from the stochiometric amount to an amount greatly exceeding the stochiometric amount, e.g. up to 20–30 times the stochiometric amount. Rather than crystallizing the hemihydrate from the aqueous solvent mixture, proper crystallization is also achieved by evaporating the organic solvent component, preferably a low-boiling one, while retaining a sufficient amount or ratio of water. The solvent may if needed, be heated to facilitate dissolution of the timolol base, and after the addition of water and possibly auxiliary solvent, the mixture is preferably stirred to facilitate the formation and crystallization of the hemihydrate. As regards the volume ratio between water and organic solvent, generally organic solvent is used in an excess. From a process technical viewpoint, a suitable ratio could be, e.g., from about 1:5 to 1:30.

The identity of crystals obtained from the different above mentioned procedures was confirmed by comparing their powder X-ray diffraction patterns.

From the above it is clear that R-timolol should inevitably form the corresponding mirror image hemihydrate in an analogous manner, however it has been unexpectedly been discovered that it does not.

The following examples illustrate exemplary procedures for synthesizing S-timolol hemihydrate.

EXAMPLE 6

S-(-)-3-morpholino-4-(3-tert-butylamino-2-hydroxypropoxy)-1,2,5-thiadiazole hemihydrate (S-timolol hemihydrate 366 g of S-timolol base are dissolved in 1.5 litres of toluene. The solution is cooled to 0° C. 175 ml of water and thereafter 875 ml of hexane are added while vigorously stirring. Crystallization sets in after approximately 30 to 60 minutes.

Thereafter stirring is continued for about 30 minutes. 25 ml of water and 1750 ml of hexane are added, whereafter mixing is continued for about 2 hours at 0° C. The precipitate is filtered and washed with appr. 300 ml of hexane. Drying is carried out at room temperature.

335 g (89%) of the title product are obtained, m.p. 48 to 50° C. (capillary tube). Optical purity 100% e.e., $[\alpha]25°/405=-16.0°$.

EXAMPLE 7

S-(-)-3-morpholino-4-(3-tert-butylamino-2-hydroxypropoxy)-1,2,5-thiadiazole hemihydrate (S-timolol hemihydrate 500 g of S-timolol maleate are weighed into a flask and 2 litres of water are added. Stirring is continued for about 10 minutes, 1 litre of toluene is added and the mixtured is cooled to about 15° C., at which temperature a 47% NaOH solution is added dropwise until the pH is about 12.5. The phases are separated. The toluene phase is recovered and the water phase is re-extracted with 0.5 litres of toluene. The toluene phases are combined and washed with water. The toluene solution is cooled to 0° C. 175 ml of water are added and thereafter 875 ml of hexane while vigorously stirring. Crystallization sets in after about 30 to 60 minutes. Thereafter stirring is continued for about 30 minutes. 25 ml of water and 1750 ml of hexane are added, whereafter stirring is continued for about 2 hours at 0° C. The precipitate is filtered and washed with about 300 ml of hexane. Drying is effected at room temperature.

335 g of the title compound are obtained (89% calculated on the S-timolol maleate), m.p. 48 to 50° C. (capillary tube). Optical purity 100% e.e., $[\alpha]25°/405=-16.0°$.

EXAMPLE 8

S-(-)-3-morpholino-4-(3-tert-butylamino-2-hydroxypropoxy)-1,2,5-thiadiazole hemihydrate (S-timolol hemihydrate 100 g of S-timolol base are dissolved in 500 ml of diisopropyl ether while boiling. 50 ml of water are added and the mixture is cooled to +10 to +20° C. 0.1 g of S-timolol hemihydrate is added as a seed while vigorously stirring. After the crystallization has set in the mixture is cooled to 0° C., at which temperature stirring is continued for 1 hour. The crystals are filtered, washed with diisopropyl ether and dried below 4° C. The yield is 81 g (79%) of S-timolol hemihydrate, m.p. 48 to 50° C. (capillary tube). Optical purity 100% e.e., $[\alpha]25°/405=-16.0°$.

I claim:

1. An Ophthalmic topical composition containing a therapeutically effective amount of (S)-(-)-3-morpholino-4-(3-tert-butyl-amino-2 hydroxypropoxy)-1, 2,5-thiadiazole hemihydrate together with an ophthalmic carrier.

2. Ophthalmic composition according to claim 1 which is in the form of solution.

3. Ophthalmic composition according to claim 1 wherein the ophthalmic carrier is water.

4. Ophthalmic composition according to claim 2 which is a unit dose form.

5. Ophthalmic composition according to claim 4 wherein the ophthalmic carrier is water.

6. Ophthalmic composition according to claim 1 which is in the form of a gel.

7. Ophthalmic composition according to claim 1 which is in the form of an oil.

8. Ophthalmic composition according to claim 1 which is in the form of an ointment.

9. Ophthalmic composition according to claim 1 which is in the form of an insert.

10. Ophthalmic composition according to claim 1 which contains 0.01 to 5% by weight of (S)-(-)-3-morpholino-4-(3-tert-butyl-amino-2 hydroxypropoxy)-1,2,5-thiadiazole hemihydrate.

11. Ophthalmic composition according to claim 10 contains 0.1 to 2% by weight of (S)-(-)-3-morpholino-4-(3-tert-butyl-amino-2 hydroxypropoxy)-1,2,5-thiadiazole hemihydrate.

12. Ophthalmic composition according to claim 1 in unit dose form consisting of (S)-(-)-3-morpholino-4-(3-tert-butyl-amino-2 hydroxypropoxy)-1,2,5-thiadiazole hemihydrate, a water carrier and buffer.

13. Ophthalmic composition according to claim 12 containing 0.001 mg to 5 mg of (S)-(-)-3-morpholino-4-(3-tert-butyl-amino-2 hydroxypropoxy)-1,2,5-thiadiazole hemihydrate.

14. Method for the topical treatment of glaucoma and ocular hypertension which comprises administering to the eye of a human or animal in need of such treatment a therapeutically effective amount of (S)-(-)-3-morpholino-4-(3-tert-butyl-amino-2 hydroxypropoxy)-1,2,5-thiadiazole hemihydrate.

15. Method according to claim 14 wherein (S)-(-)-3-morpholino-4-(3-tert-butyl-amino-2 hydroxypropoxy)-1,2,5-thiadiazole hemihydrate is administered in the form of an ophthalmic composition at a concentration of 0.01 to 5% by weight in an ophthalmic carrier.

16. Process for the pharmaceutically treating a subject with (S)-(-)-3-morpholino-4-(3-tert-butyl-amino-2 hydroxypropoxy)-1,2,5-thiadiazole hemihydrate comprising the steps of:

preparing a composition containing an intraocular pressure effective lowering amount of (S)-(-)-3-morpholino-4-(3-tert-butyl-amino-2 hydroxypropoxy)-1,2,5-thiadiazole hemihydrate; and topically applying the prepared composition to the eye of the subject.

17. Process of claim 16 wherein the step of preparing comprises admixing one or more selected adjuvants pharmaceutically acceptable for topical administration to the eye together with the (S)-(-)-3-morpholino-4-(3-tert-butyl-amino-2 hydroxypropoxy)-1,2,5-thiadiazole hemihydrate.

18. Process of claim 17 wherein the composition is formed into a dosage form.

19. A pharmaceutical composition for topical ophthalmic application to the eye of a subject containing an intraocular pressure lowering effective amount of (S)-(-)-3-morpholino-4-(3-tert-butyl-amino-2-hydroxypropox)-1,2,5-thiadiazole hemihydrate wherein the composition is in a dosage form.

* * * * *